United States Patent
Verwaerde et al.

(10) Patent No.: US 7,083,947 B2
(45) Date of Patent: Aug. 1, 2006

(54) ASSAY TECHNIQUES USING NEMATODE WORMS

(75) Inventors: Philippe Verwaerde, Neuville en Ferrain (FR); Gwladys Cuvillier, Gentbrugge (BE)

(73) Assignee: Devgen NV, Zwijnaarde (BE)

( * ) Notice: Subject to any disclaimer, the term of this patent is extended or adjusted under 35 U.S.C. 154(b) by 37 days.

(21) Appl. No.: 10/276,453

(22) PCT Filed: May 21, 2001

(86) PCT No.: PCT/IB01/01058

§ 371 (c)(1), (2), (4) Date: Jun. 6, 2003

(87) PCT Pub. No.: WO01/88532

PCT Pub. Date: Nov. 22, 2001

(65) Prior Publication Data

US 2003/0190597 A1   Oct. 9, 2003

(30) Foreign Application Priority Data

May 19, 2000   (GB) ................... 0012229.1

(51) Int. Cl.
  C12P 21/06   (2006.01)
  G01N 1/30    (2006.01)
  G01N 33/48   (2006.01)
  A61K 49/00   (2006.01)
  A01K 67/00   (2006.01)
  A01K 67/033  (2006.01)

(52) U.S. Cl. ............ 435/69.1; 435/40.5; 424/9.1; 800/8

(58) Field of Classification Search ........... 435/69.1, 435/40.5; 424/9.1; 800/8
See application file for complete search history.

(56) References Cited

U.S. PATENT DOCUMENTS 6,579,701 B1 * 6/2003 Keegan et al. ............ 435/69.1
6,787,125 B1 * 9/2004 Verwaerde et al. .......... 424/9.1

FOREIGN PATENT DOCUMENTS

| WO | WO 90/09096 A2 | 8/1990 |
| WO | WO 98/51351 A1 | 11/1998 |
| WO | WO 99/37770 A1 | 7/1999 |
| WO | WO 99/66323 A1 | 12/1999 |
| WO | WO 00/01846 A2 | 1/2000 |
| WO | WO 00/34438 A2 | 6/2000 |
| WO | WO 00/63425 A2 | 10/2000 |
| WO | WO 00/63427 A2 | 10/2000 |
| WO | WO 01/12796 A2 | 2/2001 |

OTHER PUBLICATIONS

Brownlee, D.J.A. et al., Actions of the anthelminric ivermectin on the pharyngeal muscle of the parasitic nematode, *Ascaris suum*. Parasitol. 115: 553-561, 1997.

Davis, R.E. Neurophysiology of glutamatergic signalling and anthelmintic action in *Ascaris suum*: pharmacological evidence for a kainate receptor. Parasitol. 116: 471-486, 1998.

Rand, J.B. et al., Genetic Pharmacology: Interactions between Drugs and Gener Products in *Caenorhabditis elegans*. Methods in Cell Biology 48: 187-204, 1995.

Smith, H. et al., Effect of Ivermectin on *Caenorhabditis elegans* Larvae Presiously Exposed to Alcoholic Immobilization. J. Parasitol. 82: 187-188, 1996.

Terada, M. et al., Studies in Chemotherapy of Parasitic Helminths (VIII). Effects of some Possible Neurotransmitters on the Motility of *Angiostrongylus Cantonenis*. Japan J. Pharmacol. 32: 643-653, 1982.

\* cited by examiner

Primary Examiner—Kent Bell
(74) Attorney, Agent, or Firm—Wolf, Greenfield & Sacks, P.C.

(57) ABSTRACT

Improved techniques for performing assays using nematode worms, such as nematode worms from the genus *Caenorhabditis*. The assays generally comprise exposing nematodes to at least one compound which paralyzes or kills the nematodes.

19 Claims, No Drawings

ASSAY TECHNIQUES USING NEMATODE WORMS

RELATED APPLICATIONS

This application is a national stage filing under 35 U.S.C. § 371 of PCT International application PCT/IB01/01058, filed May 21, 2001, which was published under PCT Article 21(2) in English.

The present invention relates to improved techniques for performing assays using nematode worms, such as nematodes worms from the genus *Caernorhabditis*.

In particular, the invention relates to improved techniques for performing assays using nematode worms in multi-well plate format. Such multi-well plate assays may be automated (i.e. using suitable robotics) and/or may be configured for (compound) screening medium to high throughput.

Other aspects, embodiments and advantages will become clear from the further description hereinbelow.

Techniques for performing in vivo assays using the nematode worm *Caenorhabditis elegans* (*C. elegans*) as a model organism have been described in the art, most notably in the following applications by applicant: PCT/EP99/09710 published as WO 00/34438 (15 Jun. 2000); PCT/EP99/04718, published as WO/00/01846 (15 Jan. 2000); PCT/IB00/00575, published as WO 00/63427 (26 Oct. 2000); PCT/IB00/00557, published as WO 00/63425 (26 Oct. 2000); PCT/IB00/00558, published as WO 00/63426 (26 Oct. 2000); as well as for instance PCT/US98/10080 (published on 19 Nov. 1998 as WO 98/51351), PCT/US99/13650, PCT/US99/01361 (published on 29 Jul. 1999 as WO99/37770), and PCT/EP00/05102).

As described in these applications, one of the main advantages of such assays involving the use of *C. elegans* is that they can be carried out in multi-well plate format (with each well usually containing a sample of between 2 and 500, and usually between 20 and 200 nematodes per well). Also because of this, assays involving the use of *C. elegans* can be carried out in an automated fashion, i.e. using suitable robotics (as are described in the aforementioned applications and/or as may be commercially available).

Furthermore, because assays involving the use of *C. elegans* may be automated, such assays are also ideally suited for screening of libraries of chemical compounds, in particular at medium to high throughput. Such automated screens may for instance be used in the discovery and/or development of new compounds (e.g. small molecules) for pharmaceutical, verterinary or agrochemical/pesticidal (e.g. insecticidal and/or nematicidal) use.

Generally, in the assays described above, the nematodes are incubated in suitable vessel or container—such as a compartment or well of a multi-well plate—on a suitable medium (which may be a solid, semi-solid, viscous or liquid medium, with liquid and viscous media usually being preferred for assays in multi-well plate format). The nematodes are then contacted with the compound(s) to be tested, e.g. by adding the compound to the medium containing the worms. After a suitable incubation time (i.e. sufficient for the compound to have its effect—if any—on the nematodes), the worms are then subjected to a suitable detection technique, i.e. to measure/determine a signal that is representative for the influence of the compound(s) to be tested on the nematode worms, which may then be used as a measure for the activity of the compound(s) in the in vivo assay.

Often, in particular for automated assays, such a detection technique involves a non-visual detection method, such as measurement of fluorescence or another optical method, measurement of a particular marker (either associated with worms or associated with the medium)such as autonomous fluorescent proteins (AFP's) such as green fluorescent proteins (GFP's), aequorin, alkaline phosphatase, luciferase, Beta-glucoronidase, Beta-lactamase, Beta-galactosidase, acetohydroxyacid, chloramphenicol acetyl transferase, horse radish peroxidase, nopaline synthase, or octapine synthase. For example, for automated assays carried out in multi-well plates, so called (multi-well) "plate readers" may be used for detecting/measuring said signal.

For a further description of the above and other assay techniques involving the use of nematodes as a model organism, reference is made to the prior art, such as the applications by applicant referred to above.

Although the above assay techniques are well established in the art—and have been successfully used by applicant to screen libraries comprising tens-of-thousands chemical compounds—there is a constant need to improve these assays, for example to make them even more robust and reliable. The present invention provides such an improvement, in particular in the following regard:

As assays based on *C. elegans* involve the use of a living organism, which can move around in the medium in which it is kept/maintained, the distribution of worms may not be uniform throughout the medium/container. This uneven distribution of worms may interfere with the signal that is measured and thus may affect the reliability of the assay.

This may in particular be a problem with assays that are carried out in multi-well plate format, on the one hand because such assays are often carried out in liquid or viscous medium (making it easier for the worms to move around, also in three dimensions), but also because the automated plate readers used in such assays often measure the signal from only part of the well (e.g. from the bottom part/halve of the well, from the bottom tip of the well, and/or through the central vertical axis of the well).

It has now been found that this problem may be solved—and thus the reliability of assays involving the use of *C. elegans* improved—by adding to the medium in which the nematodes are kept—e.g. after the nematodes have been suitably exposed to the compound(s) to be tested—at least one substance that paralyses the nematodes. Due to this paralysis, essentially all the nematodes present in the sample used collect at the bottom of the well, allowing for a more reliable and reproducible measurement of the signal generated by said sample (e.g. by measurement at the bottom of the well or along the central vertical axis of the well).

Thus, in a first aspect, the invention relates to a method for measuring/determining at least one signal generated by and/or associated with a sample of nematode worms, which nematode worms are kept in a suitable medium in a suitable vessel or container, said method comprising the steps of:

exposing the sample of nematodes to at least one compound which paralyses or kills the nematodes present in the sample; and measuring/determining the at least one signal.

In the method of the invention, the sample of nematodes can be kept—e.g. maintained, grown or incubated—in any suitable vessel or container, but is preferably kept in a well of a multi-well plate, such as standard 6, 24, 48, 96, 384, 1536, or 3072 well plates (in which each well of the multi-well plate may contain a separate sample of worms). Such plates and general techniques and apparatus for maintaining/handling nematode worms in such multi-well plate format are well known in the art, for instance from the applications mentioned hereinabove.

The sample of nematodes may be kept in or on any suitable medium—including but not limited to solid and semi-solid media—but is preferably kept in a suitable liquid or viscous medium (e.g. with a viscosity at the temperature of the assay that is equal to a greater than the viscosity of M9 medium, as measured by a suitable technique, such as an Ubbelohde, Ostwald and/or Brookfield viscosimeter). Again, suitable media for growing/maintaining nematode worms are well known in the art, for instance from the applications mentioned hereinabove, and include M9.

The sample of nematodes may comprise any suitable number of worms, depending on the size of the container/vessel used. Usually, the sample will comprise between 2 and 500, in preferably between 3 and 300, more preferably between 5 and 200, even more preferably between 10 and 100 nematodes. When the assay is carried out in multi-well plate format, each well usually contains between 15 and 75 worms, such as 20 to 50 worms. The medium may further contain all factors, compounds and/or nutrients required to carry out the assay and/or required for the survival, maintenance and/or growth of the worms. For this, reference is again made to the prior art, such as the applications referred to above. In one specific embodiment, the medium also contains a suitable source of food for the worms (such as bacteria). This not only ensures/promotes survival and/or growth of the nematodes, but may also trigger or increase pharynx pumping by the nematodes, and may therefore facilitate assays based on and/or requiring (at least some degree of) pharynx pumping.

The at least one compound which paralyses the nematodes may be any suitable compound which (at the concentration added to the sample of nematodes) paralyses the worms, such that they collect at the bottom of the container. Preferably, said compound is chosen from Ethanol, methanol, DMSO, Levamisole, aldicarb, azide, trichlorphon, muscimole, carbosulfan, carbofuran, carbosasos, most preferably ivermectine. Also, it is not excluded to use a compound which (at the concentration added to the sample of nematodes) kills the nematodes, although this is generally not preferred.

The paralysing compound is added to the sample of nematode worms (e.g. to the medium/container or well containing said sample) in a concentration such that—due to the paralysing effect of the compound (and usually also due to gravity)—the worms collect at a specific part of the container or well, which is usually the part from which the signal of interest generated by/associated with the sample of nematodes is measured/determined. Usually this will be the bottom half, bottom part or bottom tip of the container or well. Suitable concentrations of paralysing compound may easily be determined by the skilled person, and—depending on the compound(s) used—may be between 0.01 and 10.000 micromolar, preferably between 0.1 and 1000 micromolar, in particular between 1 and 100 micromolar. For instance, for ivermectine, a suitable concentration will usually be between 0.5 and 50 micromolar, in particular between 1 and 10 micromolar, such as 3 micromolar.

In step b) above, the worms are exposed to the at least one paralysing compound for a time that is sufficient for the worms—due to the paralysing effect of the compound (and usually also due to gravity)—to collect at a specific part of the container or well,e.g. at the bottom of the well. Suitable exposure times may easily be determined by the skilled person, and—depending on the compound(s) used—may be between one minute and four hours, preferably between 5 minutes and two hours, more preferably between ten minutes and one hour, such as between 20 minutes and 45 minutes.

Thereafter, the signal of interest generated by/associated with the sample of nematodes is measured/determined. This may be any suitable signal, such as fluorescence or another optical signal. These and other suitable signals, as well as for (automated) techniques for measuring them, reference is again made to the prior art, and in particular to the applications referred to hereinabove. Preferably said signal is measured by means of a non-visual detection technique, as described in the applications referred to above.

The method of the invention may be used to improve the reliability, reproducibility and/or robustness of any assay involving the use of nematode worms—and in particular nematode worms of the genus *Caenorhabditis* such as *C. elegans* or *C. briggsae*—such as the assays described in the applications mentioned above and other in other applications by applicant. As will be clear from the above, this may simply be achieved by adding to the method/protocol for carrying out said known assay, a step of adding the paralysing compound (i.e. step b) above), in the manner described above, and prior to measurement of the signal of interest. As will also be clear from the above, the invention is particularly suited as an improvement for such known assays when they are carried out in a multi-well plate format, in liquid or viscous medium, and/or in an automated fashion.

As will also be clear from the above, the invention may in particular be used to improve assays in which the effect of one or more compounds or other factors on (the signal generated by/associated with) the sample of nematode worms is determined, and some of these assays are also described in the applications referred to above. Generally, in such assays, the method of the invention will comprise the further step of:

exposing the sample of nematode worms to at least one compound to be tested.

The further conditions for this step a)—such as suitable concentrations of compound and times for such exposures—will depend on the specific assay used and on the compound(s) to be tested. Reference is again made to the prior art, such as the applications referred to above. The compounds may be tested at any suitable concentration or range of concentrations (e.g. to establish a dose response curve). For example, suitable concentrations may be in the range of between 0.001 and 10.000 micromolar, preferably between 0.01 and 1000 micromolar, in particular between 0.05 and 500 micromolar, although the invention is not limited thereto.

Suitable contact times of the compound and the (sample of) nematodes may be between 10 seconds and 48 hours, preferably between 1 minute and 36 hours, and may for instance be between 30 minutes and 24 hours. For instance, incubation of about 1 hr to overnight (e.g. about 16 hours) may be used.

In a further aspect, the invention relates to the use of at least one paralysing compound—as described above—in improving the reliability, reproducibility and/or robustness of an assays involving the use of (a sample of) nematode worms. In this aspect, the paralysing compound, its use and the assays involving the use of nematode worms are preferably as further described above.

Experimental Part:

This methodology as described above has been applied to a variety of assays, which resulted in enhanced reproducible read-out. More particularly the method of the invention has been applied as an improvement of the earlier described pharynx pumping assay (WO00/06327), resulting in an improved assay method. In this aspect of the invention, a method is described to identify improved signal detection in multi-well assays, using dispensed nematodes, wherein prior to detecting a signal indicating pharynx pumping by non-visual detection means, a paralyzing chemical substance is added to the wells of the multi-well plates.

An other application of this new invention related to the detection of the defecation rate, in which the improvement results in a method to identify improved signal detection in multi-well assays, using dispensed nematodes, wherein prior to detecting a signal indicating defecation by non-visual detection means, a paralyzing chemical substance is added to the wells of the multi-well plates.

In still another application of this new invention, the invention is applied to egg laying, in which the improvement results in a method to identify improved signal detection in multi-well assays, using dispensed nematodes, wherein prior to detecting a signal indicating egg laying by non-visual detection means, a paralyzing chemical substance is added to the wells of the multi-well plates.

In a further application of this new invention, the invention is applied to fatty acid uptake, and cholesterol uptake, in which the improvement results in a method to identify improved signal detection in multi-well assays, using dispensed nematodes, wherein prior to detecting a signal indicating for lipid uptake or cholesterol uptake by non-visual detection means, a paralyzing chemical substance is added to the wells of the multi-well plates In a further application of this invention a method is described to identify genetic mutations, using nematode worms dispersed in multi-well assay plates, contacted with a mutagen, wherein prior to detecting a signal indicating phenotypic, physiologic, behavioral or biochemical changes by non-visual detection means, a paralyzing chemical substance is added to the wells of the multi-well plates.

Methods to generate mutations in *C. elegans* have previously been described in "Methods in Cell Biology, Volume 48, ed. by Epstein and Shakes, Academic press". The major disadvantage of these methods is the laborious task to select for the desired mutants. The method described here allows to select in an efficient and fast way for a mutation with the desired phenotypic, physiologic, behavioral or biochemical change. The detection methods are the same as these described above and refer to the pharynx pumping assay, the defecation assay, the egg laying assay, the fatty acid uptake assay.

Finally, the further application of this invention is a method to identify RNAi knock-outs, using nematode worms dispersed in multi-well assay plates, are feeded with bacteria that express high quantities of dsRNA, wherein prior to detecting a signal indicating phenotypic, physiologic, behavioral or biochemical changes by non-visual detection means, a paralyzing chemical substance is added to the wells of the multi-well plates.

What is claimed is:

1. A method for measuring/determining at least one signal generated by/or associated with a sample of nematode worms, which nematode worms are kept in a suitable medium in a suitable vessel or container, said method comprising the steps of:
    exposing the sample of nematodes to at least one compound which paralyses or kills the nematodes present in the sample, wherein the at least one paralysing compound is ethanol, methanol, levimasole, aldicarb, azide, trichlorphon, muscimole, carbosulfan, carbofuran, carbosasos or ivermectine; and
    measuring/determining the at least one signal; which method is carried out in an automated fashion.

2. The method according to claim 1, in which the nematode worms are kept in a compartment or a well of a multi-well plate.

3. The method according to claim 1, in which the at least one signal is detected using a non-visual detection technique.

4. The method according to claim 1, in which the at least one signal is fluorescence.

5. The method according to claim 1, further comprising the step of:
    exposing the sample of nematode worms to at least one compound to be tested.

6. The method according to claim 1, in which the sample of nematodes is exposed to at least one paralysing compound at a concentration of paralysing compound(s) of between 0.01 and 10,000 micromolar.

7. The method according to claim 1, which is carried out in a liquid or viscous medium.

8. The method of claim 6, wherein the concentration of paralysing compound(s) is between 0.1 and 1000 micromolar.

9. The method of claim 8, wherein the concentration of paralysing compound(s) is between 1 and 100 micromolar.

10. A method for measuring/determining at least one signal generated by/or associated with a sample of nematode worms, which nematode worms are kept in a suitable medium in a suitable vessel or container, said method comprising the steps of:
    exposing the sample of nematodes to at least one compound which paralyses or kills the nematodes present in the sample, wherein the sample of nematodes is exposed to the at least one paralysing compound at a concentration of the at least one paralysing compound of at least 1 micromolar; and
    measuring/determining the at least one signal; which method is carried out in an automated fashion.

11. The method according to claim 10, in which the nematode worms are kept in a compartment or a well of a multi-well plate.

12. The method according to claim 10, in which the at least one signal is detected using a non-visual detection technique.

13. The method according to claim 10, in which the at least one signal is fluorescence.

14. The method according to claim 10, further comprising the step of:
    exposing the sample of nematode worms to at least one compound to be tested.

15. The method according to claim 10, in which the at least one paralysing compound is ethanol, methanol, DMSO, levimasole, aldicarb, azide, trichlorphon, muscimole, carbosulfan, carbofuran, carbosasos or ivermectine.

16. The method according to claim 10, in which the sample of nematodes is exposed to at least one paralysing compound at a concentration of the at least one paralysing compound of between 1 and 10,000 micromolar.

17. The method of claim 16, wherein the concentration of paralysing compound(s) is between 1 and 1000 micromolar.

18. The method of claim 17, wherein the concentration of paralysing compound(s) is between 1 and 100 micromolar.

19. The method according to claim 10, which is carried out in a liquid or viscous medium.

* * * * *